(12) United States Patent
Quist et al.

(10) Patent No.: US 7,072,038 B2
(45) Date of Patent: Jul. 4, 2006

(54) PARTICLE ID WITH NARROW ANGLE DETECTORS

(76) Inventors: Gregory M. Quist, 2166 Weiss Way, Escondido, CA (US) 92026; Hanno Ix, 1128 Via Valle Vista, Escondido, CA (US) 92029

(*) Notice: Subject to any disclaimer, the term of this patent is extended or adjusted under 35 U.S.C. 154(b) by 0 days.

(21) Appl. No.: 10/834,516

(22) Filed: Apr. 29, 2004

(65) Prior Publication Data

US 2004/0201845 A1     Oct. 14, 2004

Related U.S. Application Data

(62) Division of application No. 09/922,497, filed on Aug. 3, 2001, now Pat. No. 6,774,995.

(51) Int. Cl.
*G01N 15/02* (2006.01)

(52) U.S. Cl. ................................. 356/338

(58) Field of Classification Search ............ 356/39–43, 356/335–343; 422/73, 68.1, 82.05–82.09; 436/10, 63, 164
See application file for complete search history.

(56) References Cited

U.S. PATENT DOCUMENTS

| | | | |
|---|---|---|---|
| 3,770,351 A | 11/1973 | Wyatt | |
| 3,901,602 A | 8/1975 | Gravatt, Jr. | |
| 4,070,113 A | 1/1978 | Frazer et al. | |
| 4,173,415 A | 11/1979 | Wyatt | |
| 4,265,538 A | 5/1981 | Wertheimer | |
| 4,548,500 A | 10/1985 | Wyatt et al. | |
| 4,565,448 A | 1/1986 | Abbott et al. | |
| 4,728,190 A | 3/1988 | Knollenberg | |
| 4,906,094 A | 3/1990 | Ashida | |
| 4,942,305 A | 7/1990 | Sommer | |
| 4,952,055 A | 8/1990 | Wyatt | |
| 5,104,221 A * | 4/1992 | Bott et al. ................. 356/336 |
| 5,125,737 A | 6/1992 | Rodriguez et al. | |
| 5,247,340 A | 9/1993 | Ogino | |
| 5,414,508 A | 5/1995 | Takahashi et al. | |
| 5,436,465 A | 7/1995 | Borden et al. | |
| 5,534,999 A | 7/1996 | Koshizuka et al. | |
| 5,737,078 A | 4/1998 | Takarada et al. | |
| 5,999,256 A | 12/1999 | Jones et al. | |
| 6,023,324 A | 2/2000 | Myers | |
| 6,100,541 A | 8/2000 | Nagle et al. | |
| 6,118,531 A | 9/2000 | Hertel et al. | |
| 6,120,734 A | 9/2000 | Lackie | |
| 6,417,920 B1 * | 7/2002 | Shimaoka ................. 356/336 |
| 6,421,121 B1 * | 7/2002 | Haavig et al. ............. 356/338 |
| 2002/0014224 A1 * | 2/2002 | Ismailov ..................... 123/494 |
| 2002/0040851 A1 * | 4/2002 | Mc.Neil-Watson et al. . 204/549 |

OTHER PUBLICATIONS

"Discrimination Of Phytoplankton Via Light-Scattering Properties", Limnol. Oceanogr., 34(1), 1989, pp. 96-112 (American Society of Limnology and Oceanography, Inc.) By: Philip J. Wyatt and Christian Jackson.

* cited by examiner

*Primary Examiner*—Tu T. Nguyen
(74) *Attorney, Agent, or Firm*—Leon D. Rosen (57) ABSTRACT

A method for the identification of unknown particles contained in a fluid. The method utilizes a source of radiation and at least one radiation detector to measure the radiation scattered by an unknown particle in the fluid. The measurement for the unknown particle is compared with a standard radiation scattering pattern capable of uniquely identifying a previously identified particle and the unknown particle is identified based upon the comparison.

4 Claims, 8 Drawing Sheets

*Graph showing Relative Intensity vs Time for ALGAE, with multiple overlapping curves peaking around time 170–175.*

FIG. 6

*Graph showing Relative Intensity vs Time for CRYPTOSPORIDIUM PARVUM, with multiple overlapping curves peaking around time 200–205.*

PARTICLE ID WITH NARROW ANGLE DETECTORS

CROSS REFERENCE

This is a division of patent application Ser. No. 09/922,497 filed Aug. 03, 2001 now U.S. Pat. No. 6,774,995, which is copending with Ser. No. 09/988,482 filed Nov. 19, 2001 which is now U.S. Pat. No. 6,519,033.

BACKGROUND OF THE INVENTION

There has been a longstanding need for techniques to detect and identify unknown particles contained in fluid media. One example of such a need is the desire to detect and identify pathogenic microorganisms contained in water. Protozoan parasites such as *Cryptosporidium parvum* and *Giardia lamblia* have been recognized as important waterborne etiologic agents of disease after contact with or ingestion of contaminated water. *C. parvum* is of major concern because it exhibits high resistance to disinfectants at the doses routinely applied in water treatment plants, has a low infectious dose, and no drug is currently approved for prophylaxis or therapy.

Current water quality monitoring techniques for *Cryptosporidium* and *Giardia* have well-known and serious limitations. First, standard techniques—from sample collection to final identification and enumeration—can take at least a day. This delay reduces or eliminates health benefits associated with monitoring (M. J. Allen et al., *JAWWA*, September 2000). Second, these techniques are labor intensive and expensive. Third, samples are often collected discretely; so transient contamination spikes are very likely to be missed by sporadic sampling. Fourth, the accuracy of the identification techniques is unacceptably poor. For example, typical recovery and identification for two standard methods, immuno-fluorescence assay (IFA) and flow cytometry cell sorting (FCCS), is around 40% for *Giardia* and around 40–50% for *Cryptosporidium*, with high coefficients of variation and high false positive rates, primarily from benign species such as algae (*Comparative Health Effects Assessments of Drinking Water Technologies: Report to Congress*, November 1988; M. LeChevallier, *JAWWA*, September 1995, p. 54; M. Frey, C. Hancock, and G. S. Jackson, AWWARF and AWWA, 1997; J. L. Clancy et al., *JAWWA*, September 1999).

Attempts to monitor water for the presence and identity of microorganisms by light scattering have met with little success—the difficulty lies in the ability to "invert" the light scattering data to determine what particle did the scattering. The inverse scattering problem is well known in classical electromagnetic theory. Unlike the "forward scattering" problem, in which the scattered radiation is completely predictable based on sufficient information about the scattering particle, the inverse scattering problem is defined by attempting to determine the physical properties of the scattering particle from the scattered radiation. Such physical properties include, for example, size, shape, internal structure, and refractive index.

A well-known solution to the inverse scattering problem is Inverse Synthetic Aperture RADAR. RADAR waves are scattered from a moving target that changes its attitude relative to the RADAR source. Scattered phase and amplitude information is collected, and a RADAR image of the target is reconstructed using signal-processing techniques (c.f. E. F. Knott, J. F. Shaeffer, and M. T. Tuley, *Radar Cross Section*, Artech House, Inc., Norwood, Mass., 1985. P. 202).

The analogous problem in optics is more problematic, because phase information is difficult to obtain due to the short wavelengths involved. Without phase information, a rigorous analytical reconstruction of the scattering particle, particularly a complex object, such as a microorganism, becomes untenable using standard techniques.

Quist and Wyatt achieved a solution to the optical inverse scattering problem using scattered amplitudes alone in the early 1980's (G. M. Quist and P. J. Wyatt, *J. Optical Soc. Am.*, November 1985, pp. 1979–1985; U.S. Pat. No. 4,548,500). Because this technique relies upon simultaneous measurement of various scattered light angles, the technique is called the Multi-Angle Light Scattering (MALS) technique. Using a scheme called "strip maps," Quist and Wyatt demonstrated that it is possible to uniquely and rapidly characterize simple particles, such as homogeneous and isotropic spheres, homogeneous rods, and homogeneous ellipsoids, using optical data generated solely from the differential cross section (the angular dependence of the scattering amplitude) without explicit phase information. However, the strip map technique is limited to simple geometric structures.

The MALS technique has been utilized with various microparticles, including, bacteria and flyash, to produce coherent scattered light patterns with multiple nulls. In 1989, Wyatt and Jackson extended the MALS technique to classifying microbiological particles in water (P. J. Wyatt and C. Jackson, *Limnology and Oceanography*, January 1989, pp. 96–112). They demonstrated that it is possible to classify 12 distinct species of phytoplankton in seawater with a statistical confidence level of greater than 99%.

The problem of waterborne outbreaks of disease related to *Giardia* and *Cryptosporidium*, and their presence at the effluent of state-of-the-art water treatment plants complying with current regulations, clearly indicates the importance of effective real time, continuous monitoring systems to identify their presence in water. Thus, it is desirable to develop a method to identify particles in a fluid, with one example being the use of such a method to detect and identify rapidly and accurately *Cryptosporidium* and *Giardia* in drinking water.

DISCLOSURE OF THE INVENTION

The present invention provides a method for the identification of particles in a fluid. More particularly, the invention provides a method for the identification of unknown particles contained in a fluid comprising: a source of radiation and at least one detection means to detect said radiation secured in a predetermined position relative to the radiation source, positioned to sample a fluid. The fluid is interrogated by the source of radiation, and the radiation scattered by an unknown particle in the fluid is measured at the detection means. Then, the results obtained in the measurement step are compared with standard results previously obtained from an identified particle, wherein the standard results are obtained by generating a radiation scattering pattern capable of uniquely identifying the previously identified particle, and the unknown particle, is identified based upon the results of the comparison step.

In one aspect, the present invention provides a new detection and enumeration system for use in on-line, continuous, and real time monitoring of fluids for microorganisms. In this embodiment, the present invention employs a technique called multi-angle light scattering, utilized with a source of electromagnetic radiation, to provide, for example, the ability to continuously monitor the quality of drinking water. In tests performed with low turbidity water, it is found that the light scattering patterns of *Cryptosporidium, Giardia,* and a background interference organism such as algae are sufficiently unique to discriminate between the pathogens and the background. These results demonstrate that a pathogen monitoring system can be provided that is continuous, real-time, and on-line. Such a system provides a public health benefit by providing timely information to operators of treatment plants, reservoirs and distribution systems and may provide an economic benefit by enabling treatment plant operators to optimize disinfection and treatment processes.

BRIEF DESCRIPTION OF THE DRAWINGS

FIG. 2A presents a schematic diagram of one embodiment of a detection means to detect radiation scattered by a particle in accordance with the present invention, in which

DETAILED DESCRIPTION OF THE INVENTION

The present invention provides a method for the identification of particles in a fluid. More particularly, the invention provides a method for the identification of unknown particles contained in a fluid comprising a source of radiation and at least one detection means to detect said radiation secured in a predetermined position relative to the radiation source, positioned to sample a fluid. The fluid is interrogated by the source of radiation, and the radiation scattered by an unknown particle in the fluid is measured at the detection means. Then, the results obtained in the measurement step are compared with standard results previously obtained from an identified particle of the same type, wherein the standard results are obtained by generating a radiation scattering pattern capable of uniquely identifying the previously identified particles, and the unknown particle is identified based upon the results of the comparison step.

Unless otherwise indicated, the following terms will have the following meanings:

The term "radiation" will be taken in its broadest sense to include any form of energy or particle transmitted from its source by a surrounding medium. Most commonly, but without limitation, the forms of radiation found useful in the present invention will include electromagnetic radiation, such as light and microwaves, radioactive emissions, such as $\alpha$, $\beta$ and $\gamma$ emissions, and acoustic radiation, such as sound waves. The particular form of radiation selected will depend, at least in part, on the nature of the particle that is sought to be detected and identified.

The term "detect" will be taken in its broadest sense to include any means to sense the presence of the thing sought. In the present invention, a detection device will commonly include the ability to respond to and measure the radiation from the scattering source.

The term "radiation scattering pattern" will be taken in its broadest sense to include any set of data that is generated as a result of detecting the radiation scattered by a particle of interest when the particle is subjected to the influence of a source of radiation.

The term "identify" will be taken in its broadest sense to include any means of detecting and classifying a particular particle and assigning it to a specific particle type, and uniquely distinguishing it from particles of a different type. In the case of microorganisms, it may be sufficient to classify the particles by genus, by genus and species, by genus, species and strain, or some alternative form of classification.

The term "interrogate" will be taken in its broadest sense to include any means by which a fluid that may contain a particle of interest is subjected to the influence of a source of radiation.

The term "measure" will be taken in its broadest sense to include any quantification of the existence or magnitude of the detected radiation.

The term "fluid" will be taken in its broadest sense to include any medium having the property of flowing, including both gaseous and liquid media.

The term "particle" will be taken in its broadest sense to include any object of matter of sufficient size to be capable of being distinguished from the fluid medium. Particles will typically be a member of a particular type of particle, capable of being distinguished from particles of other types. In certain embodiments of the present invention, the particles will be biological, such as microorganisms, and each type of microorganism will typically constitute a separate species, or an identifiable strain of a species.

The term "algorithm" will be taken in its broadest sense to include any clearly specified process for computation, that is, a set of rules that, if followed, will give a prescribed result. Examples of algorithms include, without limitation, multiple analysis of variances (MANOVA), neural networks, simulated annealing, algorithm-independent machine learning, fuzzy logic, grammatical methods, and other techniques for pattern recognition.

In one aspect, embodiments of the present invention provide a new detection and enumeration system for use in on-line, continuous, and real time monitoring of fluids, such as water, for the presence of particles, such as specific microorganisms. In this aspect, for embodiments involving the use of electromagnetic radiation to detect particles in liquids, the present invention employs a technique called multi-angle light scattering (MALS), utilized with a source of electromagnetic radiation, to provide, for example, drinking water quality monitoring. In tests performed with low turbidity water, it is found that the radiation scattering patterns (RSPs) of *Cryptosporidium, Giardia,* and various species of algae commonly misidentified as *Cryptosporidium* in standard tests, are sufficiently unique to discriminate between the pathogens and the background algae particles. These results demonstrate that a pathogen monitoring system can be provided that is continuous, real-time, and on-line. Such a system provides a public health benefit and can enable treatment plant operators to optimize disinfection and other treatment processes, thereby saving treatment costs.

In such embodiments, a device useful for the gathering of data can be constructed in accordance with teachings well known in the art. For example, a device useful in the practice of the present invention can be constructed generally in accordance with U.S. Pat. No. 4,548,500, the relevant portions of which are incorporated herein by this reference. Additional devices that can be adapted to the practice of the present invention include devices disclosed in U.S. Pat. Nos. 5,125,737 and 5,808,738, the relevant portions of which are incorporated herein by this reference. Similar such devices can also be obtained commercially, for example, as the DAWN Model B MALS Measurement System available from Wyatt Technology Corporation, Santa Barbara, Calif.

The present invention will now be described hereinbelow, and with reference to the drawings, in which FIG. 1 shows a schematic block diagram of the major components 10 of an embodiment of the present invention that utilizes electromagnetic radiation and the MALS technique. Referring to the FIG. 1, a pipe 12 containing a stream of water to be analyzed by the present system is depicted, together with another pipe or container device 15 where water is diverted from out of the stream. Water in container device transparent walls 15 can be provided under pressure from the stream of water in the pipe 12, or can require pumping. In addition, it is possible to analyze water at a location in the pipe 12. A portion of the detecting apparatus 16 (colloquially termed the "read head") can be positioned external to pipe 12, or can be submerged within pipe 12 directly into the water stream so the light beam passes through the walls by passing through a hole in the walls. One embodiment provides that the system be maintained external to the water and measuring a "side stream" of water. Water that is sampled by the detecting apparatus 16 typically constitutes only a small portion of the water that is passing by the sampling point 14, and may optionally not be returned to the original stream.

The detecting apparatus 16 depicted in FIG. 1 provides a source of electromagnetic radiation 17, for example a coherent light source, such as a laser, to provide illumination and interrogation of the fluid (see FIG. 2A). In certain embodiments, the light source is a single laser at a fixed wavelength, but in general, one can utilize multiple light sources, or a single light source with several discrete (or continuous) wavelengths. The laser produces a beam 13 that passes through transparent walls 15 of a pipe or other container device that contains a liquid 19 such as water with particles in it. The laser beam pass through a detect zone 18 that lies along the beam. Light which encounters a particle in the detect zone 18, is scattered and a portion of the scattered light is directed into discrete detectors 24 which measure the intensity of the scattered light.

The electro-optical detectors 24, which generate analog optical signals, and which can be of the type illustrated at 112 in FIG. 2B, detect only light from the small detect zone 18, and do not detect light from outside the detect zone. The detect zone 18 is spaced from the transparent walls 15 by more than the length of the detect zone along the laser beam. The signals generated by the detectors are amplified to a useful level. These signals are either processed by local electronics, or sent via a transmission means 28 (FIG. 1) to a local or remote processor, such as a personal computer, or workstation 30 (FIG. 1). The information can be sent via wired or wireless communications, and can be processed by a base station computer, or can be sent via other means (e.g. a network of linked digital computers) to a remote processor.

Real-time information regarding the status of the water passing through the present detection system can then be provided to a user interface, and displayed for observation by a user of the system. Alternatively, the system can provide warning signals, e.g. optical, electronic, or acoustic signals, to a local or remote user, indicating that there is a detection of a particle or several detections of the same particle.

Processing of Information from the System

The present invention is generally, though not exclusively, used in two forms First, it is used in the generation of RSPs of a desired "target" microorganism, such as *Cryptosporidium parvum*. There is no practical limit to the type of particle or variety of particles that can be identified using this system. The performance of the system scales with wavelength and the size of the particle, and there is no intrinsic need to limit this technique to light as a form of electromagnetic radiation, nor to electromagnetic radiation as a form of radiation. Other forms of radiation, such as radioactive emissions, and acoustic radiation, such as SONAR, can be employed in the practice of the invention.

Second, once the RSPs are generated, the invention is used to detect and identify the particles whose RSPs are stored in memory, either in the local electronics, or in the supported computers, such as those discussed previously.

Generation of Radiation Scattering Patterns

FIG. 3 shows a schematic diagram of the data flow through a specific embodiment of the system for the generation of radiation scattering patterns (RSPs). A sample of the target microorganism is introduced into a fixture that contains the read head (the radiation source and the detection apparatus). Raw data is collected from the read head by a commercial data acquisition program such as LabView (by National Instruments), operating on computer 30 (FIG. 1). The raw data is generated from the optical signals as described above and represented in FIG. 4.

An analog to digital (A/D) circuit translates the analog electrical signals into digital signals that are then stored by the computer. Sixteen channels are typically used as a matter of convenience, as the 16-channel configuration is typical for A/D's available commercially, and in a representative embodiment of the invention, 16 photodetectors (e.g. photomultiplier tubes or solid state detectors such as photodiodes) are utilized for convenience. However, other configurations are easily adopted, i.e. a greater or lesser number can be used.

Typically, particles are only rarely passing through the laser beam for test particle concentrations of approximately 200 microorganisms/mL or less. The passage of each such particle is termed an "event." The raw data collected by the system includes all channel data amplitudes as a function of time for the duration of the test session.

Figure 3:
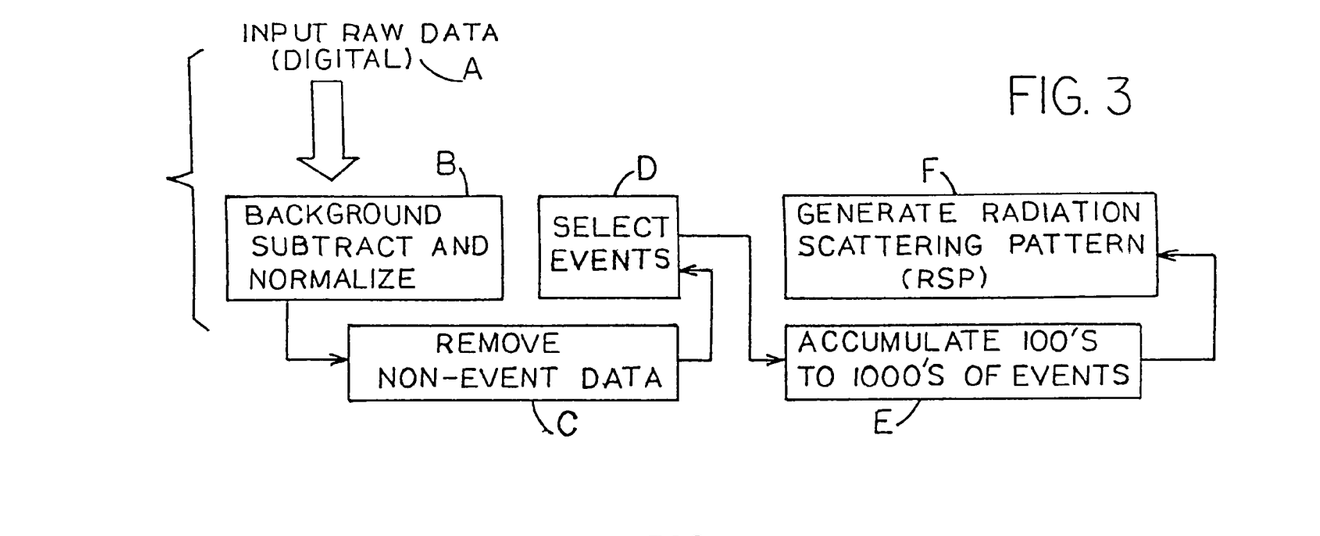
FIG. 3 presents a schematic block diagram of the data flow for the generation of a radiation scattering pattern in one embodiment of the present invention.
Figure 4:
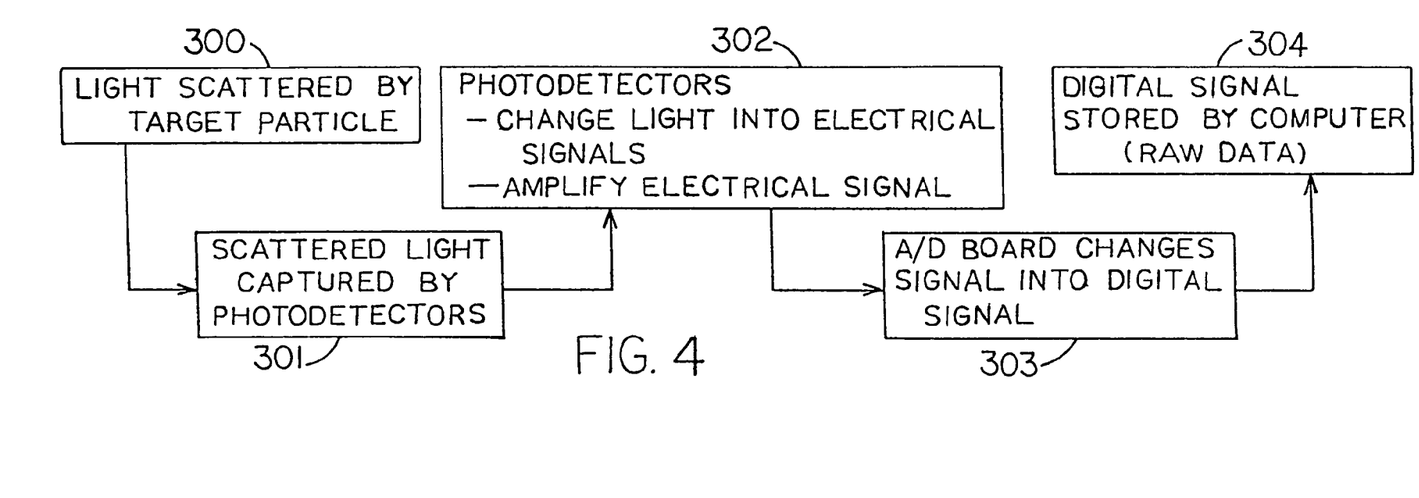
FIG. 4 presents a schematic block diagram of the collection of data for the generation of a radiation scattering pattern in one embodiment of the present invention

Referring again to FIGS. 3 and 4, data is collected and initially processed by subtracting out the background scatter for each channel. Then each channel is normalized through data taken prior to the test measurements on a solution of isotropic scattering particles, such as dextran, or small polystyrene latex spheres. The non-event data, which generally occupies most of the time of a measurement session, is removed by a simple criterion, such as whether a single channel has a signal "n" times the AC noise level above zero (since the background is subtracted). The value n can be selected as desired in order to maximize the benefit obtained from the application of the technique. Values of n greater than 2 have been found useful.

Further analysis is conducted of the absolute and relative strength of a signal in order for the signal to be considered meaningful. This further analysis precludes the consideration of partially illuminated oocysts, of foreign bodies too large or too small, or of optical and electronic artifacts.

The data recorded from all channels during an event are kept in memory, and the non-event data are discarded. Events are then selected from the stored data, based on a criterion that: (a) a trigger channel, chosen to be one of the channels, has a signal above a level of "m" times the AC noise level, and (b) several other channels also have coincident signals above background during this same event time period. The value m can be selected as desired in order to maximize the benefit obtained from the application of this technique. Values of m greater than 2 have been found useful. In addition, there are various other schemes that can be used.

Figure 1:
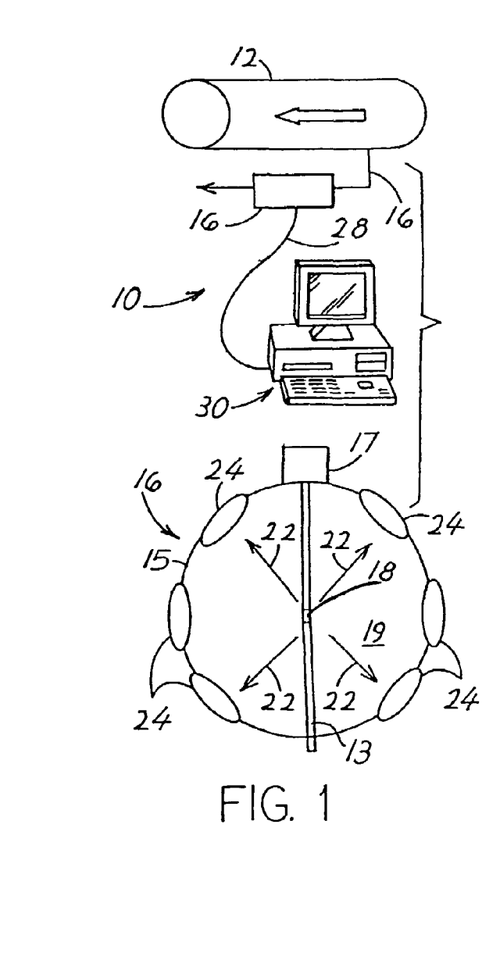
FIG. 1 presents a schematic block diagram of the major components of one embodiment of the present invention.

Due to the intensity profile of the laser beam, each of the signals generated by the electro-optical detector 24 (FIG. 1) resembles a Gaussian bell curve. When all 16 data channels are displayed simultaneously, a family of 16 bell curves appears for each scattering event. These bell curves differ mostly in their amplitude and to a minor degree in the relative position of their maximums. Therefore a scattering event can be rather accurately described by the values of the amplitude maximums alone.

Once an event is located, the maximum values of all channels during that event are stored. Thus, an event is described by a set of 16 numbers. Hundreds to thousands of events captured in this manner are then stored as representative of the sample being measured. The data collected in this manner are then used to generate the RSP of the microorganism under analysis.

Details of the Generation of the Radiation Scattering Pattern

The event data are represented by matrices of numbers. Each matrix row represents an event, and each column represents the signal amplitude as discussed. To establish specificity, one such matrix is produced for each of particle types A, C, and G (algae, *Cryptosporidium,* and *Giardia* respectively). However, despite all practical precautions taken, a certain percentage of contamination data in each matrix must be expected. It is in the mutual correlation of the 16 matrix columns, and the variation of this correlation From matrix A to C to G, where the desired information is found.

The RSP is generated as follows (representative of numerous ways such a pattern can be established): First, measurements are made of all of the selected types of particles/microorganisms in the manner discussed above. In addition, measurements are also made of other particles that are expected to provide interference to the measurements. Next, the logarithm of the data values for each event is taken. Then, all of these measurements are submitted to a pattern recognition algorithm, such as a multiple analysis of variances analysis (MANOVA), for at least a subset of the 16 data channels of the system. MANOVA is a well-known statistical technique that finds the optimum linear combinations (the "canonical space") of channels such that the data is optimally grouped amongst like particle types and maximally separated from distinct particle types in the MANOVA canonical space. In this way the measurement data are subjected to an algorithm that enhances the separation of data generated from measurements of the target particles from data generated from measurements of distinct particles. Generally, application of MANOVA to the measurement data provides distinction but not clear separation of the different particles types from each other. Therefore, further refinement of the RSP may be desirable.

In such a case, a numerical technique (colloquially called the "Wall") is optionally applied in order to further enhance the separation of the measurement data generated from a particular particle type from the measurements from data generated from distinct particle types. The "Wall" is an erasure set technique that searches each of the points in the MANOVA canonical space for all of the samples and requires that "N" nearest neighbors must be of the same type. If they are not, then this data point is eliminated from the developing RSP. If this criterion is satisfied, then the data point is retained and becomes part of the first order RSP of the target particle type. The value N can be selected as desired in order to maximize the benefit obtained from the application of the technique. Values of N between 1 and 20 have been found useful.

Thereafter, a further criterion can be applied to refine the particle type-specific RSP even further. For each point in a particle type RSP, the average distance in the MANOVA canonical space to all points of its like particle type is calculated, and if a point is greater than "x" times the mean distance, it is rejected and the remainder of the points are taken to define the particle type-specific RSP. The value x can be selected as desired in order to maximize the benefit obtained from the application of the technique. Values of x greater than 1 have been found useful.

Particle Identification

Once specific RSPs have been developed for each of the types particles, then the measurements taken from unknown particles can be compared against the established RSPs as follows: First, the unknown particle event is processed as described earlier. The logarithm of the 16 channel values is taken. These values are then translated into the MANOVA canonical space by the linear transformation defined by the MANOVA that generated the RSPs to begin with. Once in MANOVA canonical space, the particle value point is tested against the established particle type-specific RSPs by calculating the average distance between the unknown point and "z" points of the RSP to which the unknown particle is compared. The value z can be selected as desired in order to maximize the benefit obtained from the application of the technique. Values of z between 1 and 20 have been found useful. If the average distance is less than "y" times the average for the RSP itself, then the particle is identified positively with that particle type RSP. The value y can be selected as desired in order to maximize the benefit obtained from the application of the technique; values of y between 0.5 and 10 have been found useful.

Details of the Analysis of the Signals

The signal analysis from the light scattering amplitudes primarily follows the classical procedure of MANOVA. This technique is frequently used, for instance, for automatic pattern recognition. MANOVA's concept is the detection and separation of multiple modes in the distributions of the data. The representation of one event composed of 16 channel data, i.e. one matrix row, can be thought of as a point in a 16 dimensional data space. Accordingly, an entire matrix of data can be thought of as representing a data cloud in 16 dimensional (16D) space. That is, the density of such a cloud in 16D space is the multi-dimensional equivalent of a Gaussian distribution in 1 dimensional space. To the extent that one can recognize distinct data clouds, specificity can be established. In addition, by recognizing order, the dimensionality may be reduced without loss of specificity. MANOVA is frequently capable of reducing the original number of dimensions to a smaller number without losing significant information about the specificity of the data. In one embodiment of the present invention, MANOVA will reduce the data from 16D to 3D space without losing information about the origin of the data (i.e. the type of particle).

An algorithm such as MANOVA can be easily executed by computers using pre-programmed software, for example, by using the well-known software MATLAB (The MathWorks) on personal computers. Each dimension is an optimally weighted composition of the original data. Therefore it is further possible to investigate the significance of information provided by a particular data channel. Frequently, several channels are redundant. Therefore, they can either be turned off or re-positioned so as to gather additional information.

In summary, with certain embodiments of the invention, the problem to be solved is: Given an event, i.e. a matrix row of 16 numbers, determine from what type of particle the event originated. First, the data clouds can be represented as very dense kernels close to the center of the canonical data space and low density in the far fields. This highly unequal density makes the proper separation of data points difficult. Therefore, it is deemed important to find a means of equalizing the density. This can be achieved by simply taking the logarithm of the data and applying MANOVA to the transformed data.

Next, the problem of overlap of the three data clouds in the canonical space can be overcome. This overlap is a result of similar events stemming from different particle types and sub-optimal detector placement and therefore causes errors or uncertainties in the conclusions and assignment of particle identity. One representative technique in further refining the invention is to establish "Walls" between the data clouds in the MANOVA canonical space where all data points are simply removed. The "Walls" are established by demanding that a data point be surrounded by a substantial number of the same type in order to be considered a valid point. This procedure produces a compact data space for each type within which there is little doubt to what type a particular data point belongs. The "Walls," however, reduce the yield in the operation of the apparatus; i.e. when the invention decides the decision is most likely correct and assigns an identity to an unknown particle.

At this point, in many cases the present invention would not assign any identity at all. However, it can be demonstrated that repetitions of the scattering measurements will decrease the risk that a particle will escape detection. Such repetitions can be arranged in space and/or in time. If the number of repetition of measurements for a particular unknown particle is larger than a certain value, both the yield will increase and the error rate will decrease. The optimal number of repetitions is a function of the yield achieved by a single measurement.

DESCRIPTION OF A SELECTED EMBODIMENT

In order to explain certain aspects of the invention in greater detail, a description of the invention is provided for a simplified embodiment of the invention that involves the use of electromagnetic radiation to detect and identify selected types of microorganisms in supplies of drinking water.

Figure 2A:
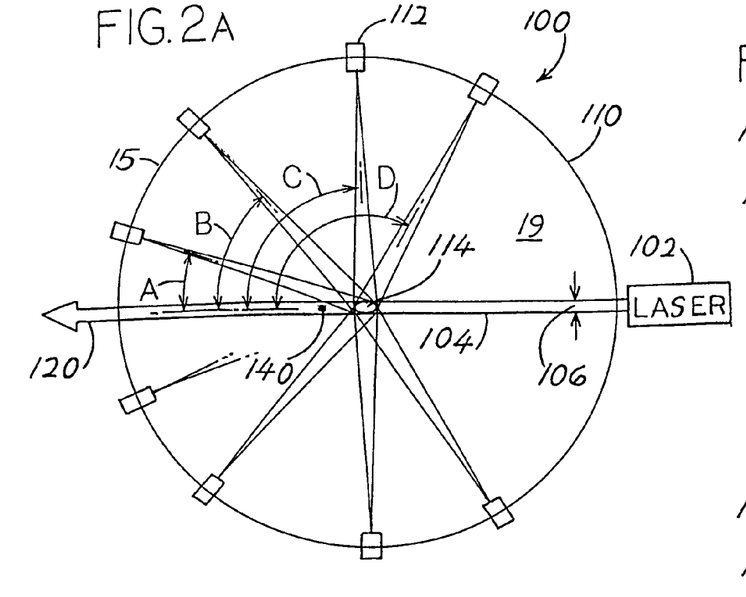
Figure 2B:
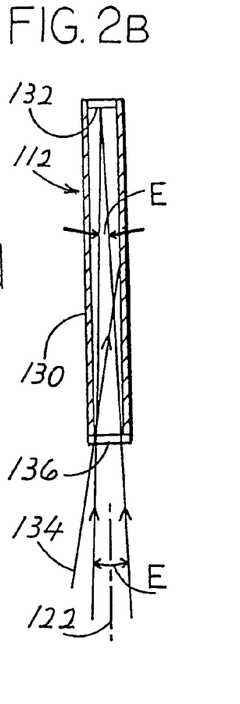
FIG. 2B depicts a single detector.

For example, FIG. 2A illustrates a system 100 for identifying such particles. The system includes a radiation source 102 which is, e.g. a laser that generates a thin collimated laser beam 104. The laser beam, or light beam passes through a liquid such as water containing particles, that lies within the transparent walls 15. In this embodiment it is preferred to use electromagnetic radiation in a range between and including ultraviolet to infrared, with the particular beam 104 being linearly polarized light having a wavelength of approximately 685 nm. The microorganism particles to be detected will have a diameter in the range of about one to thirty wavelengths (about 0.7 to 20 microns). The beam projected by the radiation source is narrow, having a width 106 of approximately 0.1 mm. A detector support framework 110 supports a plurality of detectors 112 in a fixed relationship to the radiation source, with each detector oriented to detect light emitted from a limited detect zone 114 intersected by the laser beam 104. Each detector 112 is spaced about 60 mm from the detect zone 114. The detectors are located at different angles (e.g. A-D in FIG. 2) from the forward direction of travel of the laser beam 104. FIG. 2B shows one of the detectors 112, depicting how it detects light received through a narrow angle E (such as 2.5°) from the direction 122 in which the detector is aimed. The detector includes an elongated narrow tube 130 with an inside surface that absorbs red light. A photodetector 132 lies at the distal end of the tube. Light traveling along a path indicated at 134 (outside the narrow detection angle) will strike the inside of the tube 130 and be absorbed there, so it will not impinge on the photo detector 132; only light within the narrow angle E will be detected by the photo detector 32. It is also noted that a polarizing filter 136 lies over the end of the tube, to admit only light polarized in a certain direction, for example a vertical direction.

Referring again to FIG. 2A, it can be seen that when a particle enters the detect zone 114, light from the laser beam 104 that encounters the particle will be scattered, refracted and reflected from the particle and a portion of that light may be detected by one or more of the detectors 112. A particle at a location such as 140 that is not in the detect zone 114, will disperse (scatter, refract and reflect) light, but such light will reach the detectors 112 only at angles from their direction of viewing outside of angle E and will therefore not be detected by detectors.

Figure 2C:
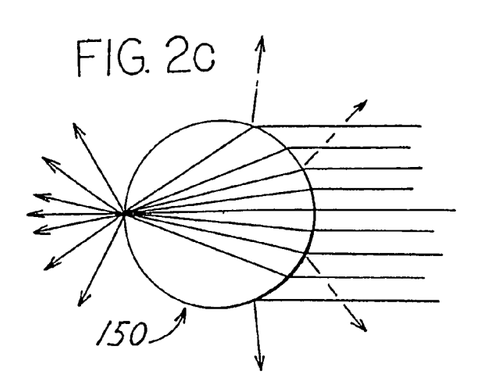
FIG. 2C depicts the interrogation of a spherical particle.

FIG. 2C illustrates the manner of dispersal of light from the laser beam 104 when it strikes a small transparent homogeneous spherical particle 150. FIG. 2H shows the hypothetical dispersion of a laser beam, by showing variation in detected light intensity as a function of angle from the direction of the beam, for a small spherical particle. The particle is a polystyrene latex sphere having a diameter of approximately 993 nm (0.993 micron), and the laser beam has a wavelength of approximately 685 nm. FIG. 2H includes two graphs, with one graph 152 representing vertically polarized light (for the laser beam and for the detectors) and graph 154 representing horizontally polarized light. It is noted that dispersion can change the polarization of the light for non-spherical particles, and only those components of polarization that are parallel to the polarization direction of the detector filter 136 will pass through and be detected. Because of the symmetrical nature of a sphere, the sphere 150 of FIG. 2C should uniformly illuminate detectors that are similarly angled and in the same plane, such as detectors DN and DP (FIG. 2F). Detectors DM and DP lie in a different plane and may be differently illuminated due to polarization effects.

FIG. 2F is an isometric view of the detection system 100 that includes two rings 170, 172 resulting in four quadrants 181, 182, 183, 184. Sixteen detectors labeled DA–DP are provided, with four detectors at each quadrant. In one example, four detectors DA–DD on each quadrant are spaced by an angle A (FIG. 2) of 20° from the laser beam forward direction 120, four others DE–DH are spaced an angle B of 50°, four others DI–DL are spaced at an angle C of 90° and four others DM–DP are spaced at an angle D of 120° from the forward direction 120.

Figure 2D:
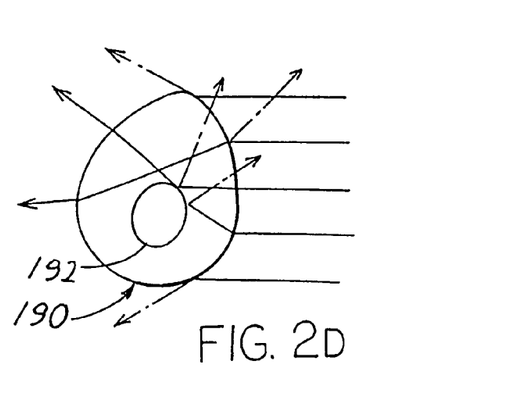
FIG. 2D depicts the interrogation of a "pear" shaped particle.
Figure 2E:
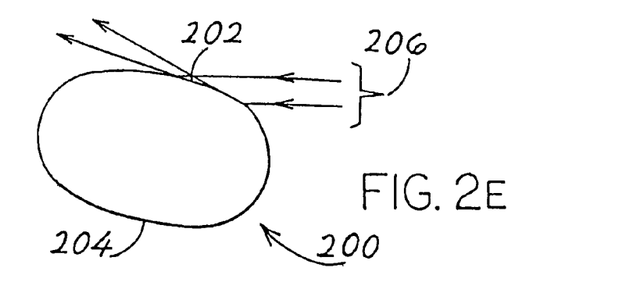
FIG. 2E depicts the interrogation of an "ovoid" shaped particle.
Figure 2F:
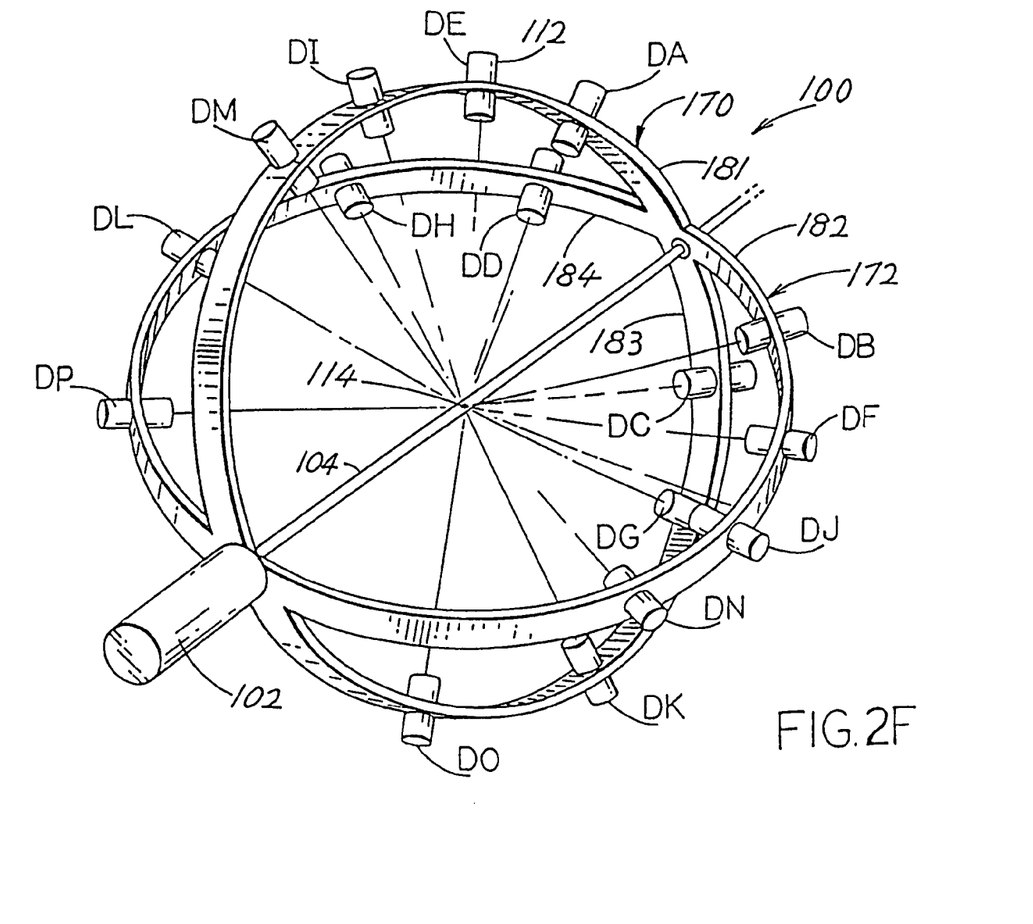
FIG. 2F is an isometric depiction of one embodiment of an apparatus according to FIG. 2A.

FIG. 2D shows a particle 190 of generally "pear" shape, with a smaller, discontinuous sub-region 192 (e.g. a cell nucleus) embedded within the particle 190. The particle 190 will disperse light primarily to one side and perhaps least to the opposite side, depending on its orientation. Also, dispersion (scattering, refraction and reflection) by an elongated object tends to change the polarization of the light. FIG. 2E illustrates another particle 200 of high refractive index such that light does not penetrate far into the particle and generally "ovoid" shape, which has opposite sides 202, 204 that are almost flat (large radius of curvature). This results in considerable light 206 at one side being directed primarily toward one detector.

In accordance with the invention, a radiation scattering pattern (RSP) is created for a particular type of particle, such as a particular pathogenic bacterium that might be found in water. First, a large number (usually at least hundreds, occasionally thousands, perhaps as many as millions) of that type of pathogen particle is introduced to water that is otherwise free of all particles. Then, the particles are allowed to pass through the beam 104, with the frequency of such events increased by increased speed of the fluid. The output signals of each of the sixteen detectors are stored each time light from the laser is detected, which indicates that a particle has entered the detect zone (an event). In one example, perhaps one hundred particles are detected every minute. The occurrence of a particle entering the detect zone is herein referred to as an event. The output signals from all of the detectors, such as sixteen output signals resulting from an event, is herein referred to as an eventvector.

Figure 2G:
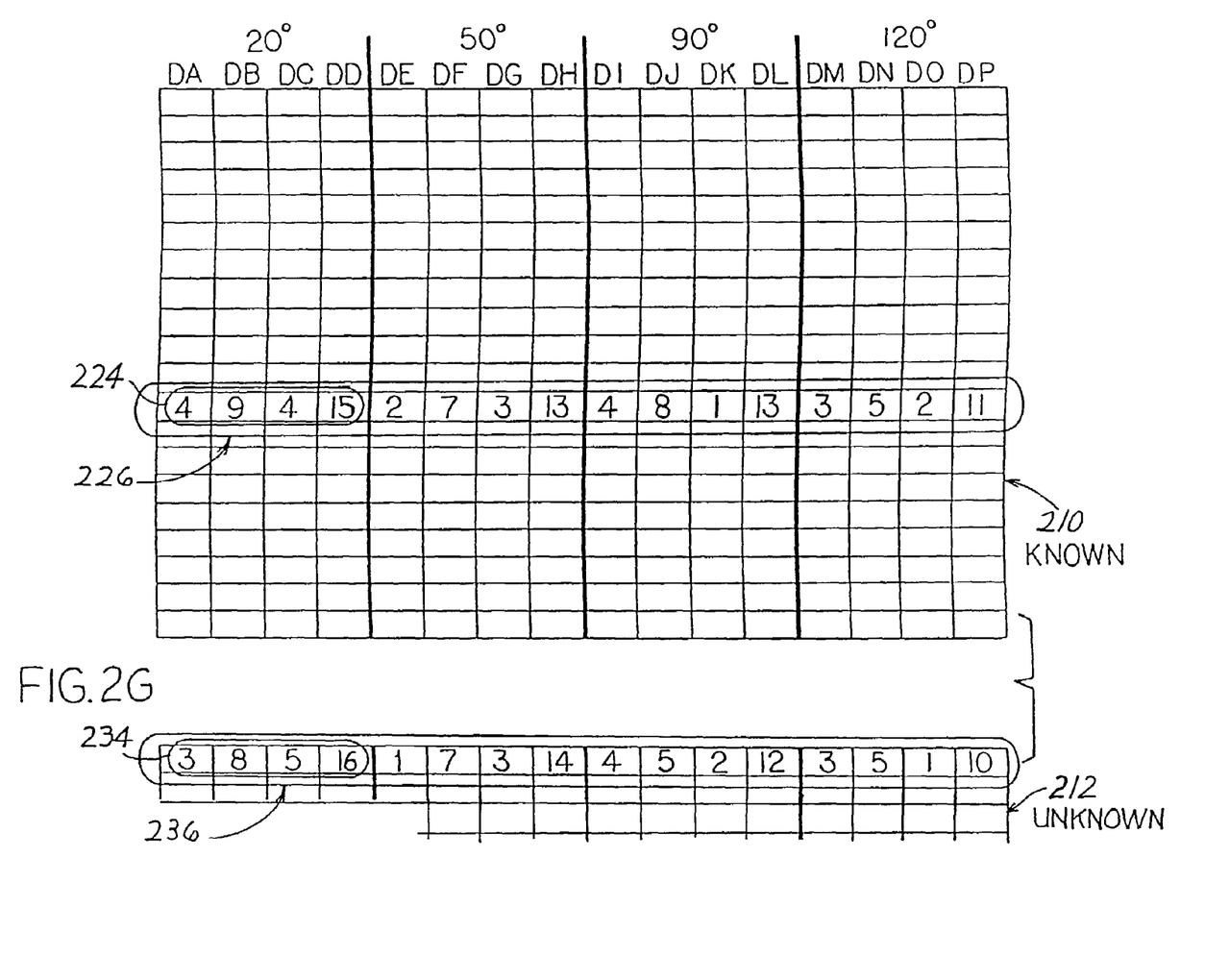
FIG. 2G depicts data memory obtained from the interrogation of a number of particles, and FIG. 2H graphically depicts the data expected to be obtained by the interrogation of a spherical particle correlated to the angle of the detector to the radiation beam.
Figure 2H:
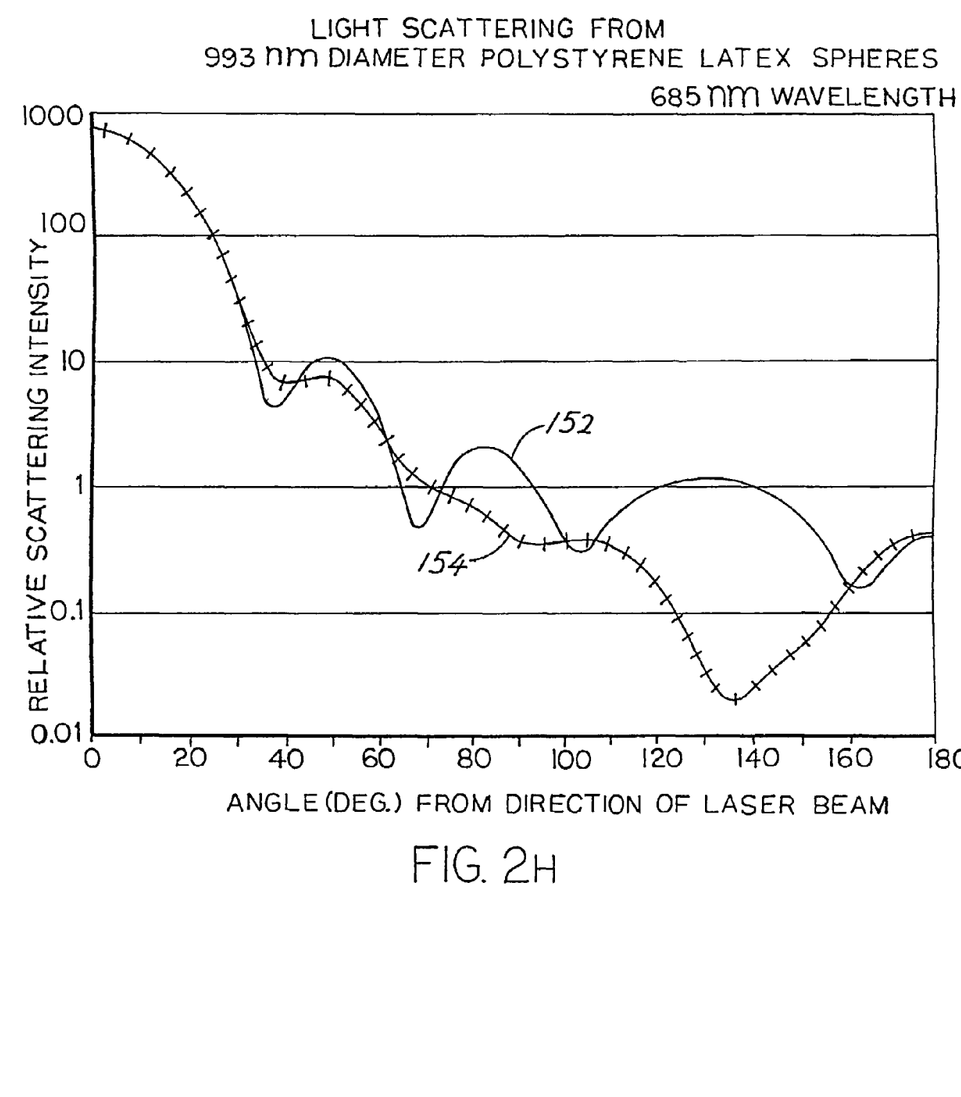

In FIG. 2G, one group 210 of boxes holds a memory that represents numerous detections of a known specie of a particle, such as a pathogen. The group of boxes includes many rows, with each row containing sixteen boxes DA–DP that represents the output of each of the sixteen detectors (a sub-pattern) each time a particle is detected in the detect zone. Although only twenty rows are shown, an analyzing circuit preferably contains many more (e.g. hundreds or thousands). The data stored in group 210 represents the basis for the RSP for that particular pathogen. Each row of 16 outputs represents the dispersion characteristics for each of different variations of a species (e.g. that vary slightly in size and shape), and for each of numerous different orientations with respect to the laser beam 104 for each variation of the species.

This data is then processed by subjecting the data as a whole to an algorithm, such as MANOVA, which enhances the separation of data generated from these particle-type measurements from data generated from measurements of distinct particles, and further by subjecting the data obtained from the algorithm to a mathematical technique that eliminates the data generated from each particle unless the particle is of the same type as the N particles whose generated data is most similar to that particle's data, where N is a whole number greater than 0. The resulting data is the RSP for that particle type.

The system is then used to identify unknown pathogens that may have contaminated water, such as a drinking water supply of a city. The same apparatus 100 of FIG. 2F is used to interrogate a sample of the water (typically a continuous stream) and the laser is continually energized to interrogate the unknown particles. Every time an unknown particle enters the detect zone 114, resulting in light being detecting by a plurality of detectors, the outputs of the sixteen detectors are recorded to produce an unknown sub-pattern, or eventvector. The data is then processed in the same manner as the data used to generate the particle type specific RSPs. In effect, the circuit which records the output of the detectors for an unknown particle, determines if the sub-pattern in each row of memory 212 for one unknown particle, matches one of the numerous sub-patterns in memory 210 for a known particle species. This matching is repeated for each of several other known pathogen species whose pattern has been recorded in another memory similar to memory 210.

In FIG. 2G, memory 210 represents the many sub-patterns (sixteen numbers which are the outputs of the sixteen detectors DA–DP when one particle is interrogated) recorded for a particular known specie. An example is the particle 200 of FIG. 2E. As mentioned above, the particle 200 has a flattened surface portion 202 which may reflect considerable light to one of the four detectors DA–DD which are each angled 20° from the laser beam forward direction. For memory 210, a loop is depicted at 224 to point out data where only one of the detectors DA–DD has recorded a high light level (it varies between 1 and 16, with 16 being maximum level), which may indicate a particle with a flattened surface. The entire sub-pattern 226 includes sixteen values.

For the recordings in memory 212 of FIG. 2G, a loop is depicted around a group of numbers at 234 of the sub-pattern 236 that appear to have the same characteristics. The sub-patterns 226, 236 of the known and unknown particles have other characteristics in common, such as a high (but decreasing) number in all detectors DD, DH, DL, DP located along one sector, and moderate numbers in detectors DB, DF, DJ, DN in an opposite sector. If many of such characteristics are detected for an unknown particle sub-pattern in memory 212, which closely correspond to one or more sub-pattern for the known specie of particle in memory 210, then this indicates that the unknown particle closely matches the known particle type and that the unknown particle is presumptively of the type of pathogen that has the RSP present for the particular known particle type.

In accordance with the invention, the RSPs for many different types of known pathogens that are likely to be encountered in a city water supply are recorded, and used to determine which, if any, of those many known pathogens closely corresponds to the unknown particle. The output of the comparison can be a signal that indicates the degree of correlation of the unknown particle with the closest one of the known particles. The output can indicate that the unknown particle is of a certain type when there is a high correlation. Although a circuit could be utilized that compares known data (for a known pathogen) with new data (for an unknown pathogen), the present invention can use existing circuitry which searches for patterns in two groups of data (the sub-pattern of an unknown particle with each of the many sub-patterns of a known particle), or correlation between the two groups of data, to determine whether there are very close patterns.

It is noted that in a city water supply, one might expect to detect (interrogate) many particles that are not pathogens, before detecting a particle that is a pathogen and whose sub-pattern closely matches one of the known-particle patterns that are stored in the known-particle memories. After a large number of particles are detected and at least several of hundreds of particles are detected that closely match the known-particle pattern for one particular species, one can begin to be confident that the particular known-particle species is present in the city water supply.

Experimental Procedure

In the experimental disclosure which follows, all weights are given in grams (g), milligrams (mg), micrograms (µg), nanograms (ng), or picograms (pg), all amounts are given in moles, millimoles (mmol), micromoles (µmol), nanomoles (nmol), picomoles (pmol), or femtomoles (fmol), all concentrations are given as percent by volume (%), proportion by volume (v:v), molar (M), millimolar (mM), micromolar (µM), nanomolar (nM), picomolar (pM), femtomolar (fM), or normal (N), all volumes are given in liters (L), milliliters (mL), or microliters (µL), power ratings are given in milliwatts (mW), and linear measurements are given in millimeters (mm), micrometers (µm), or nanometers (nm), unless otherwise indicated.

*Cryptosporidium, Giardia,* and Algae Samples

Samples of the two pathogenic microorganisms to be evaluated using the present invention, *Cryptosporidium parvum* oocysts and *Giardia lamblia* cysts, and the background interference particle, an algae species *Oocystis minuta,* are provided by Dr. Jennifer Clancy of Clancy Environmental Consultants. Each of the samples has a concentration of approximately $10^7$ cells/mL. Microscopic examination of each of the samples precedes the measurements in order to verify the concentration of the samples, to reject samples that had significant clumping generally due to age, and to qualitatively observe the individual organisms to improve consistency of samples.

Sample Preparation

The water into which the Laser Toller is submerged is very low particulate water, to provide a clean background or "blank." This low particulate water is produced by passing standard tap water through a water conditioner, a carbon filter to eliminate chlorine, a single pass reverse osmosis unit, and finally through a series of filters with decreasing porosity: 200 nm, 100 nm and 50 nm. This produces water with less than about 10 particles of size 200 nm or larger per cubic centimeter.

The Laser Toller unit is submerged into a large glass test vessel containing about 60 L of very low particulate water. Prior to introducing target particles into the test vessel, a "blank" measurement is taken to ensure that the water is clean and generally without extraneous particles. Such extraneous particles may enter the water through a number of means, including dust particles, particles from the surface of the Laser Toller, or contamination of the low particulate water from algae growth.

A concentrated sample of the target particles (approximately $10^7$ particles per mL) is then pipetted into the test vessel. The final concentration of target particles is about 200 target particles/mL. Then, the water is agitated by a magnetic stir bar to create a water speed of about 1 cm/sec at the laser beam. This particle concentration and flow speed produces about 100 to 1000 events per hour. Multiple particle events create potential interference in the single particle detection, are easily identifiable, and are screened out of the data.

Measurement Apparatus

Light scattering measurements are performed using an open ring-shaped structure, colloquially termed the "Laser Toller," (P. J. Wyatt and C. Jackson, *Limnology and Oceanography,* January 1989, pp. 96–112), as depicted schematically in FIG. 2F. The Laser Troller uses a 25 mW solid state, linearly polarized laser (685 nm wavelength) as its light source and fiber optic cables to transfer light signal to detectors such as photomultipliers or photodiodes. These cables are held in place by a set of circular rings that position the 16 fiber optic cable ends on a sphere at predetermined angles surrounding the scattering region, with the ends of the fibers about 6 cm from the scattering center of the laser beam. The cable ends each have optics that provide analyzers and restrict the field of view of the fibers to about 2.5° full angle.

The Laser Troller assembly is completely submerged in water. Prior to making measurements, the Laser Troller is calibrated, and gains of each of the 16 electro-optical channels are normalized using a solution of dextran particles. Particle measurements are performed by introducing target particles into the water and stirring the water with a magnetic stir bar such that the target particles pass through the laser beam and scatter light. The scattered light signals 300 (FIG. 4) are captured by the fiber optic cables 301 and transferred to photomultiplier tubes (PMTs) 302 that amplify and convert the optical scattering amplitude into an analog electrical signal. The analog output of the Laser Troller is transmitted to an analog-digital conversion printed circuit board 303, where the analog signals are digitized. These digital signals are then transferred to a local central processing unit (CPU) 304, where the signals are analyzed.

Generation of the Radiation Scattering Pattern

Samples are individually pipetted into the test vessel, and measurements are made over two hours. This procedure generates 841 *Cryptosporidium* measurements, 782 *Giardia* measurements, and 798 algae measurements.

The maximum values for each channel during a measurement event is corrected by background subtraction and normalized, and multiple particle events are rejected (approximately 1% of the events collected are multiple events). Data are collected by the 16 detectors into 16 independent channels, each channel representing an individual scattering angle. The detectors span the range between 20° and 120° from the forward scattering angle. The maximum values for each of the channels during an event are stored in the local CPU.

Once the data is collected for each of the samples, *Cryptosporidium, Giardia,* and algae, a subset of the total data is used to generate the radiation scattering pattern. 580 total measurements of each of the microorganisms are filtered by the analysis process, ultimately resulting in an radiation scattering pattern consisting of 242 *Cryptospo-*

Figure 5:
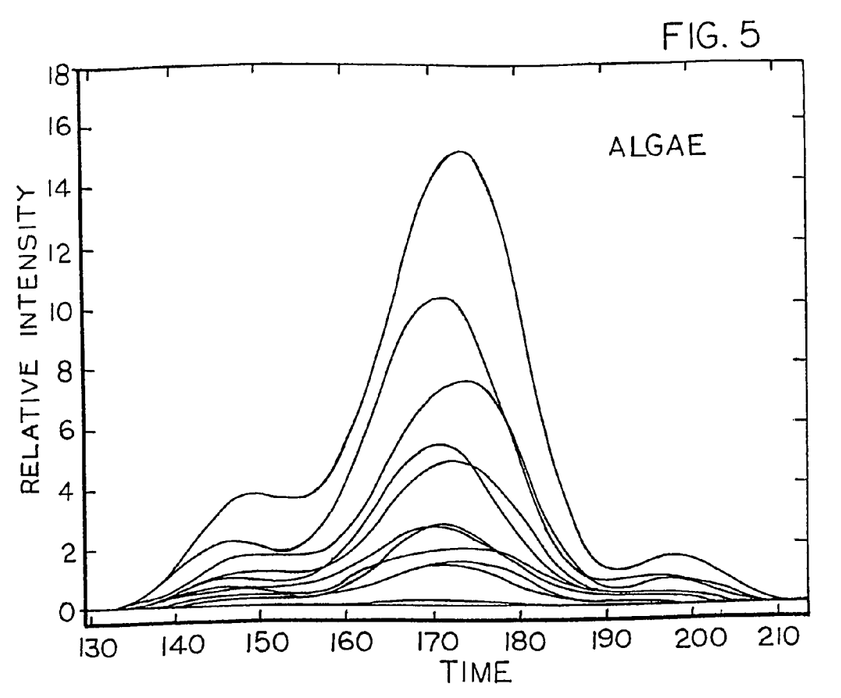
FIG. 5 presents a graphic representation of scattering data obtained using algae in the embodiment of FIG. 2A.
Figure 6:
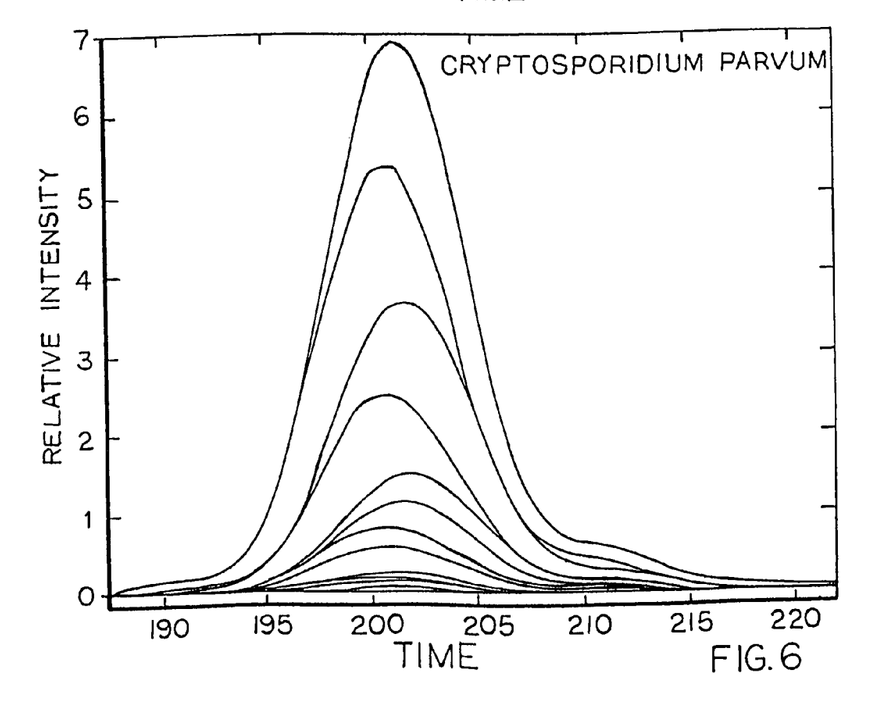
FIG. 6 presents a graphic representation of scattering data obtained using *Cryptosporidiun parvum* in the embodiment of FIG. 2A.
Figure 7:
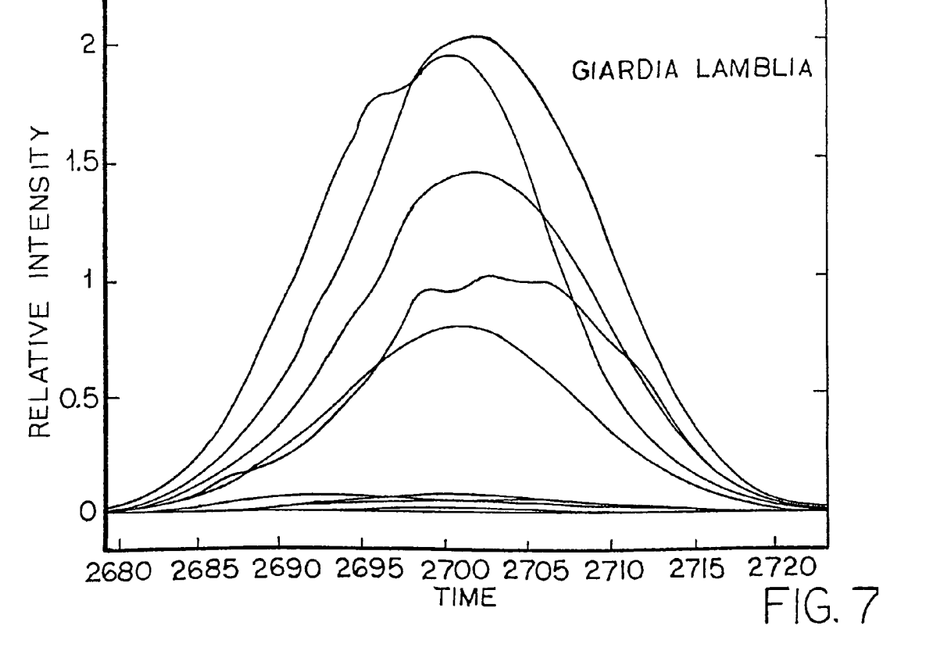
FIG. 7 presents a graphic representation of scattering data obtained using *Giardia lamblia* in the embodiment of FIG. 2A.
Figure 8:
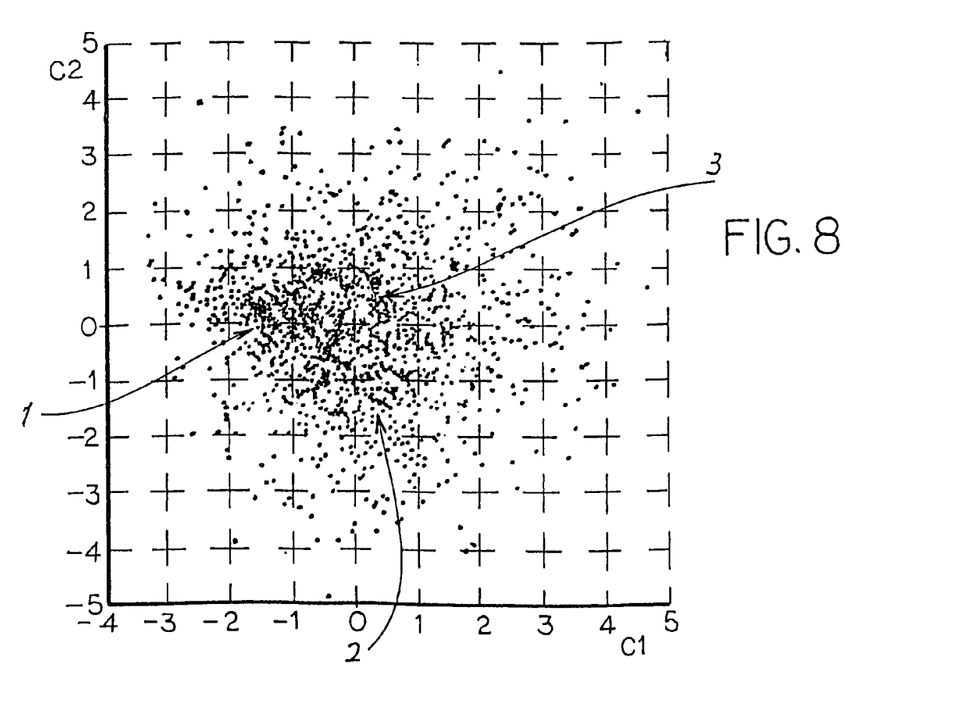
FIG. 8 presents a two dimensional projection of a radiation scattering pattern provided in accordance with the present invention.
Figure 9:
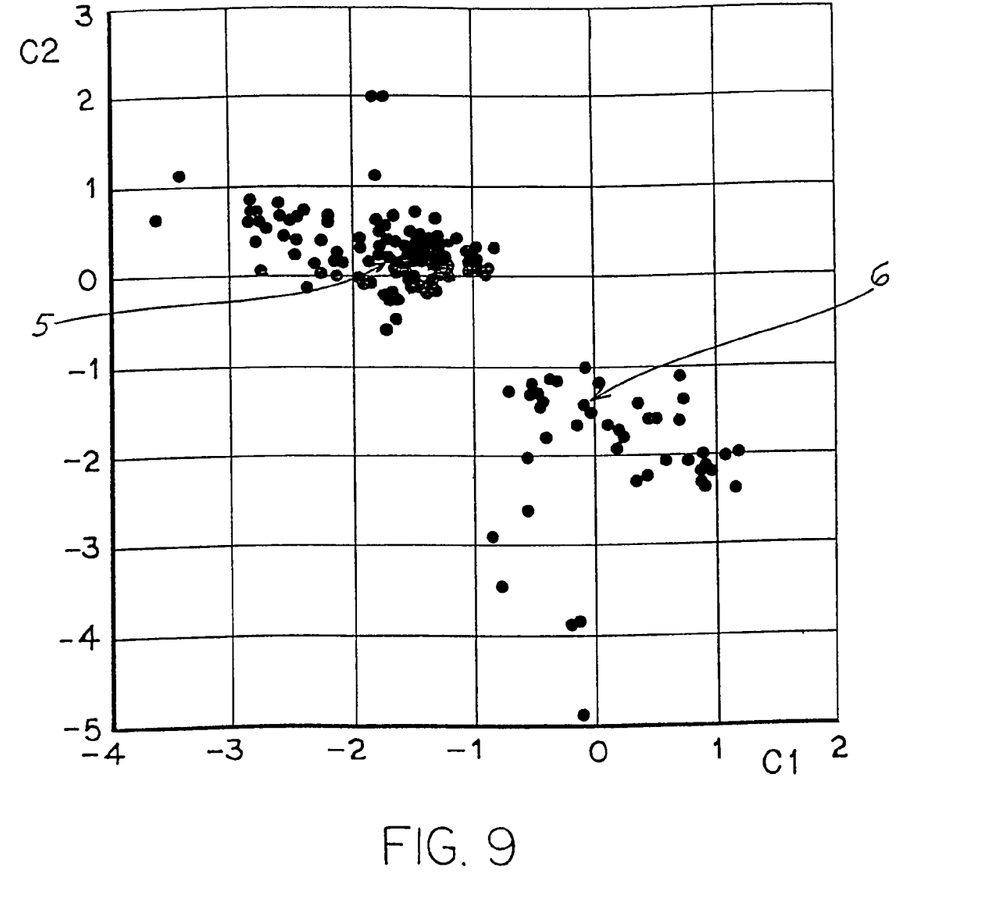
FIG. 9 presents a two dimensional projection of a refined radiation scattering pattern provided in accordance with the present invention.

*ridium* measurements and 90 *Giardia* measurements. The remainder of the measurements are used to test the effectiveness of the generation of the radiation scattering pattern. Representative examples of raw data are shown in FIGS. 5, 6 and 7.

The particle type-specific radiation scattering pattern is produced as follows: The logarithms of the data maxima are taken for each of the measurements. This modified data is then submitted to a standard statistical algorithm, called multiple analysis of variance (MANOVA). The routine used is part of a statistical package provided by MATLAB (The MathWorks). MANOVA automatically finds the linear space, as a function of the original 16 channels, in which the variance amongst targets of the same type is minimized and the variance between different targets is maximized. This linear space (the canonical space) is, in general, of lower dimensionality than the original space. For the data presented here, the original 16-dimension space is reduced to three dimensions. The results for the data, prior to applying the technique described above as the "Wall," for the *Cryptosporidium* oocysts, *Giardia* cysts, and algae are shown in a two dimensional projection in FIG. 8.

In general, due to variations among the particles of the same type, as well as variations in background scattering, impure samples, and the like, there will be significant variation in the radiation scattering patterns within a target group. These variations create overlap in the MANOVA results such that the groups, in general, will not be completely distinct (this effect is shown clearly in FIG. 8). Rather, the data will preferentially occupy one region in canonical space over others. However, this preferential region may not be sufficiently distinct to identify the targets from each other and the background particles with a high degree of confidence. A further processing step may then be utilized.

For each data point (which includes the target particles of interest and all of the background particles), a ranking of the nearest neighbors in canonical space is made. For these measurements, if the 15 nearest neighbors are of the same type, then that data point is retained. If any of the 15 nearest neighbors is of another type, then that data point is rejected. This technique creates a barrier between the points of one particle type in the canonical space and other types, and thereby generates a unique radiation scattering patterns for each particle type in the MANOVA canonical space. It should be noted that all of the algae (the interference particle) data have been removed using this algorithm, leaving *Cryptosporidium* measurements and *Giardia* measurements that are fully separated and distinct. It is this collection that defines the radiation scattering pattern of *Cryptosporidium* and *Giardia* in the MANOVA canonical space.

The *Cryptosporidium* and *Giardia* RSPs can then be further refined as follows: For each point within a given microorganism's radiation scattering patterns, the average distance between this point and the rest of the points in the radiation scattering pattern is calculated. Thus the distribution of "average distances" for all of the points in the radiation scattering pattern can be calculated. Any individual point that has an average distance more than two standard deviations than the group as a whole is rejected as an "outlier" and not included in the refined radiation scattering pattern. FIG. 10 shows the result of applying such the previously described steps, leaving a total of 242 *Cryptosporidium* measurements and 90 *Giardia* measurements in the RSP.

The RSP data, which consists of the positions in canonical data space of the data points, shown for example in FIG. 10, and the matrix of MANOVA coefficients is stored in a computer storage medium, such as a personal computer. The average distance between points in this refined radiation scattering pattern is calculated for each target particle group and used in the identification step, outlined in the following.

Identification

Measurements of *Cryptosporidium* oocysts, *Giardia* cysts, and algae, taken from the same physical samples as those used to generate the RSP, are analyzed as follows in order to demonstrate the ability of the present invention to identify these microorganisms and distinguish them from each other under controlled conditions.

A 16-channel scattering intensity matrix, derived from the maxima of each of the channels during the time an "unknown" particle (chosen from the *Cryptosporidium, Giardia,* or algae measurements) passed through the laser beam, is generated. This 16-channel measurement data is then corrected for background and normalized. As in the generation of the RSP described above, the logarithm of each of the 16 scattering intensities is taken. These intensities are then transformed into the three dimensional MANOVA canonical space, where their position in this space is compared to the previously generated type-specific radiation scattering patterns for *Cryptosporidium* and *Giardia.*

The unknown particle's position in canonical space is then compared to each of the target particle positions to determine if the unknown particle belongs to any of the target particle groups. This is performed by taking the distance, in canonical space, between the unknown particle and the three nearest particles of a target group. For example, if the total distance between the unknown particle and the three nearest *Cryptosporidium* points is less than 4.2 times the average distance between the *Cryptosporidium* data points, then the particle is identified as *Cryptosporidium.* If the total distance between the unknown particle and the three nearest *Giardia* points is less than 1.74 times the average distance between the *Giardia* data points, then the particle is identified as *Giardia.* These specific threshold values and the number of nearest particles are optimized empirically to minimize false positive identifications, that is, misidentifying algae as either *Cryptosporidium* or *Giardia.*

Results

An experimental test set of 580 each of *Cryptosporidium, Giardia,* and algae measurements are tested using the RSPs developed for *Cryptosporidium* and *Giardia.* Three criteria are used to quantify the performance of the identification:

The "Identification Rate," which is the ratio of the number of each species that are correctly identified relative to the total number of each that is measured.

The "Identification Confidence," which is the probability that a positive identification of *Cryptosporidium* or *Giardia* is correct.

The "False Positive Rate," which is the rate at which algae background is mistakenly identified as either *Cryptosporidium* or *Giardia.*

A measurement treated as an unknown is either identified positively as *Cryptosporidium* or *Giardia,* or is rejected as "unknown".

|  | Cryptosporidium | Giardia |
| --- | --- | --- |
| Identification Rate | 41.7% | 15.5% |
| Identification Confidence | 99.31% | 99.66% |
| False Positive Rate | 0% (<0.17%) | 0% (<0.17%) |

These results reflect the analysis of blind measurements compared to the RSP for a single pass through the present detection system. This procedure produced a compact data space for each type of microorganism within which there is little doubt to what type a particular data point belongs. The application of the "Wall" technique, however, reduces the yield in the operation of the apparatus, i.e. when the present invention decides the decision is most likely correct. At this point, in many cases the system would not make any decision at all. However, it can be demonstrated that repetitions of the measurement will decrease the risk that a specimen will escape detection. Such repetitions can be arranged in space and/or in time. It is true that an incorrect arrangement can deteriorate the error probability severely. However, if the false positive rate is sufficiently low, as it is in this case, and if the number of repetition of measurements is larger than a certain number, both the yield will increase and the error rate will be reduced. The optimal number of repetitions is a mathematical function of the yield achieved by a single measurement.

For the above results, it is easily shown that seven measurements of the *Giardia* and three of the *Cryptosporidium* increases the Identification Rate to greater than 70%, far beyond current state of the art.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

The invention claimed is:

1. A method for identifying unknown particles that are present in a fluid that lies in a containing device that has transparent walls, which includes interrogating particles by directing a light beam (104) of small width (106) through the fluid and detecting scattered light by a plurality of detectors (112) as a result of a single event, which is when a single particle passes through a detect zone (114) that lies along said beam, and recording the outputs of said detectors for a single event to produce an eventvector, which includes producing multiple ones of said events for particles that are of a known first species to produce multiple ones of said eventvectors for that known first species, producing an event for an unknown particle of an unknown species to produce an eventvector for the unknown particle, and comparing the multiple eventvectors for said known first species to said eventvector for the unknown species to determine whether the unknown particle is of said known first species, characterized by:

said step of directing the light beam includes directing the light beam through locations in said fluid that are not in said detection zone, so light is scattered by particles passing through locations in said fluid that lie along said light beam, that are not in said detect zone;

said step of detecting scattered light by a plurality of detectors, includes detecting, by each of said detectors, only light that is scattered from said detect zone but not light that is scattered from locations along said light beam that lie in said fluid but that are outside said detect zone, where said detect zone is spaced from said walls of said container device by more than said beam width (106).

2. The method described in claim 1 wherein:

said laser beam moves in a predetermined beam direction, said detect zone has a limited length in a direction parallel to said beam, and said detect zone is spaced from said transparent walls by more than the length of said detect zone along said beam direction.

3. Apparatus for detecting particles that are present in fluid that lies between transparent walls of a container device, which includes means for generating a light beam that passes through said walls, and a plurality of detectors that each detects light scattered from a detect zone (114) lying along the beam portion passing between said walls when a particle enters the detect zone, characterized by:

said detect zone is spaced from both of said walls, and said detectors detect only light scattered by a particle lying in said detect zone but not light from locations outside said detect zone.

4. The apparatus described in claim 3 wherein:

said detect zone is spaced, along said light beam, from said transparent walls, by more than the length of said detect zone along said light beam.

\* \* \* \* \*